United States Patent [19]

Kanschik-Conradsen et al.

[11] Patent Number: 5,463,135
[45] Date of Patent: Oct. 31, 1995

[54] FLUORINATED BENZILS AND A PROCESS FOR THEIR PREPARATION

[75] Inventors: Andreas Kanschik-Conradsen, Garbsen; Theodor Papenfuhs, Frankfurt am Main, both of Germany

[73] Assignee: Hoechst Aktiengesellschaft, Frankfurt, Germany

[21] Appl. No.: 147,826

[22] Filed: Nov. 4, 1993

[30] Foreign Application Priority Data

Nov. 4, 1992 [DE] Germany .......................... 42 37 200.3

[51] Int. Cl.$^6$ .............................................. C07C 49/784
[52] U.S. Cl. .......................... 568/331; 568/316; 568/332; 568/306; 558/415
[58] Field of Search ........................... 568/316, 331, 568/306, 332, 331; 558/415

[56] References Cited

U.S. PATENT DOCUMENTS

| | | | |
|---|---|---|---|
| 3,979,576 | 9/1976 | Janson ...................................... | 219/489 |
| 4,008,232 | 2/1977 | Lacefield ................................ | 260/247.1 |
| 4,124,726 | 11/1978 | Hamazaki et al. ...................... | 568/331 |
| 4,144,726 | 11/1978 | Kuesters et al. ........................ | 568/331 |
| 4,453,009 | 6/1984 | Yamaguchi et al. .................... | 568/316 |
| 4,612,322 | 9/1986 | Ogata et al. ............................. | 568/331 |
| 4,950,795 | 8/1990 | Husler et al. ............................ | 568/331 |

FOREIGN PATENT DOCUMENTS

| | | | |
|---|---|---|---|
| 745657 | 6/1970 | Belgium ................................. | 568/331 |
| 0101760 | 2/1986 | European Pat. Off. . | |
| 0214565 | 8/1986 | European Pat. Off. ................. | 568/316 |
| 0227088 | 7/1987 | European Pat. Off. . | |
| 0191185 | 3/1990 | European Pat. Off. . | |
| 2732149 | 2/1978 | Germany . | |
| 3420743 | 12/1985 | Germany . | |
| 3637156 | 10/1986 | Germany . | |
| 3600891 | 7/1987 | Germany . | |
| 60-72885 | 4/1985 | Japan . | |
| 1265052 | 3/1972 | United Kingdom ................... | 568/316 |

OTHER PUBLICATIONS

European Search Report No. 93117299.1, Dec. 15, 1993.
Chemical Abstract, vol. 076, No. 9, Feb. 28, 1972, No. 041832.
Chemical Abstracts, vol. 117, No. 23, Dec. 7, 1972, No. 2333927.
Chemical Abstracts, vol. 077, No. 23, Dec. 4, 1972, No. 151617.

(List continued on next page.)

*Primary Examiner*—James H. Reamer
*Attorney, Agent, or Firm*—Connolly and Hutz

[57] ABSTRACT

Fluorinated benzils and a process for their preparation A process for the preparation of fluorinated benzils of the formula (1)

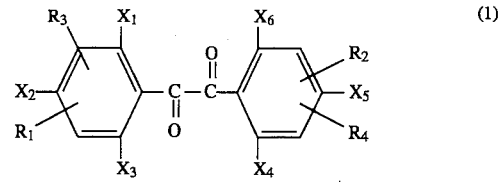

in which $X_1$–$X_6$, $R_1$, $R_2$, $R_3$ and $R_4$ are hydrogen, fluorine, chlorine or bromine atoms, or alkyl($C_1$–$C_{10}$), phenyl or naphthyl groups which may be substituted, or are groups reducing the electron density, at least one of the substituents $X_1$–$X_6$ being a fluorine atom, by reacting 1 mol of a benzil of the formula (1), in which $X_1$–$X_6$ and $R_1$ and $R_2$ have the abovementioned meanings, with the proviso that at least one of the substituents $X_1$–$X_6$ is a chlorine atom, with about 0.8 to about 2.5 mol of potassium fluoride, rubidium fluoride, cesium fluoride or tetraalkyl ($C_1$–$C_{18}$)-ammonium fluoride per chlorine atom to be exchanged, at temperatures of from about 100° C. to about 280° C., possibly in the presence of a phase transfer catalyst and a dipolar aprotic or nonpolar solvent, and the new benzils prepared by this process.

10 Claims, No Drawings

OTHER PUBLICATIONS

J. Med. Chem. 31 (1988) 983–991.
J. Org. Chem. 23 (1958) 1539–1541.
Jule. Chem. Acta 38 (1955) 46, 66.
J. Org. Chem. 23 (1958), 1306.
J. Am. Chem. Soc. 69 (1947) 667.
Advanced Org. Chem. J. Mar., 3rd Edition, 1985, 969.
Synthesis 1983, 169–184 "Alkali Metal Fluorides . . . ,",
Yakobson et al, (Mar. 1983).
Chemical Abstract, vol. 75, No. 9, J. Md. Chem. 71, vol. 14 (11) pp. 1138–1140 Un. Tehran (1971).
Chem. Abstract vol. 117, No. 23, Tetrahedron 92, vol. 48, pp. 7265 74 Univ. Liverpool, (1992).
Chemical Abstract vol. 77, No. 23, J. Chem. Soc. Perkin Trans. 1 (JCPRB4), 72 (19) pp. 2426–2429 Univ. Durham (1973).

FLUORINATED BENZILS AND A PROCESS FOR THEIR PREPARATION

The present invention relates to a new and advantageous process for the preparation of fluorinated benzils by halex (chlorine-fluorine) exchange reaction from the corresponding chlorinated compounds, some of which are new.

Fluorine-containing benzils are intermediates in the preparation of pharmaceutical active ingredients. Thus, for example, 4,4'-difluorobenzil is used to prepare antiinflammatory compounds (U.S. Pat. Nos. 4,008,232; 3,979,576). In addition, benzils can be converted, by cleaving the central C—C bond by, for example, oxidation with atmospheric oxygen (DE-A 2 732 149), into two benzoic acids which may be different and of which one contains at least one fluorine atom which has been introduced in the context of the process according to the invention. This is a possible route to, for example, valuable trihalobenzoic acids, such as 2-chloro-4,5-difluorobenzoic acid or 2,4,5-trifluorobenzoic acid, which are used as precursors to antibacterial agents (EPA 227 088; DE-A 3 600 891; DE-A 3 420 743; EP-A 191 185; JP 60 072 885; J. Med. Chem. 31, (1988), 983–991).

Such compounds have previously been prepared in a variety of ways from starting compounds which already contain fluorine. Thus, for example, 2,2'-difluorobenzil can be prepared by benzoin condensation from 2-fluorobenzaldehyde with subsequent oxidation (J. Org. Chem. 23, 1958, 1539–1541). The use of fluorinated benzaldehydes makes this synthesis route uneconomic and hence unattractive. 4,4'-Difluorobenzil can be obtained by, for example, a five-stage synthesis from fluorobenzene and chloral (Helv. Chim. Acta 38 (1955), 46, 66; J. Org. Chem. 23 (1958), 1306; J. Am. Chem. Soc. 69 (1947) 667). Due to the large number of stages, the use of cyanides, and the use as starting material of fluorobenzene—which depending on the market situation may be difficult to obtain and/or available at unfavorable cost—this synthesis route is costly and unsuitable.

There was therefore a considerable demand for a more favorable synthesis route.

Halex (chlorine-fluorine) exchange reactions in chlorinated benzaldehydes have been known for a number of years (DE-A 3 637 156). The preparation of fluorinated benzophenones, for example 4,4'-difluorobenzophenone, by halex reaction is also known in principle (EP 101 760). By contrast, the preparation of fluorinated benzils by this synthetic principle has not been described up to now. The main reasons which may account for this are described briefly below. It has long been known from the literature that aromatic α-diketones, when treated with bases, are rearranged to give α-hydroxycarboxylic acids (benzil-benzilic acid rearrangement, Advanced Organic Chemistry, J. March, 3rd Ed., J. Wiley ed., N.Y. (1985), 969). However, since alkali metal fluorides in aprotic systems are very strong bases (Yakobson et al., Synthesis (1983), 169), there was a definite possibility for the reaction of, for example, 4,4'-dichlorobenzil with an alkali metal fluoride to lead not to the desired 4,4'-difluorobenzil but instead at least partially to undergo a side reaction to give 4,4'-dichlorobenzilic acid fluoride or its secondary products.

It has now been found that, surprisingly, benzils of the formula

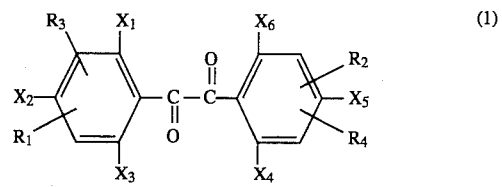

in which $X_1$, $X_2$, $X_3$, $X_4$, $X_5$, $X_6$, $R_1$, $R_2$, $R_3$ and $R_4$ are hydrogen, fluorine, chlorine or bromine atoms, alkyl($C_1$–$C_{10}$) groups, alkoxy($C_1$–$C_4$) groups, substituted or unsubstituted aryl groups such as, for example, phenyl or naphthyl groups which may be substituted by fluorine, chlorine or bromine atoms, or by alkyl($C_1$–$C_4$), alkoxy ($C_1$–$C_4$), nitro, cyano, —CHO, —COCl, —COF, —CF$_3$, —SO$_2$-alkyl(C$_1$–C$_4$), —SO$_2$F, —SO$_2$Cl, —COO-alkyl ($C_1$–$C_4$), —CON(alkyl($C_1$–$C_4$))$_2$, —CO-phenyl or —SO$_2$-phenyl groups, or groups reducing the electron density, such as, for example, nitro, cyano, —CHO, —COCl, —COF, —CF$_3$, —SO$_2$-alkyl ($C_1$–$C_4$), —CO$_2$F, —SO$_2$Cl, —CON(alkyl($C_1$–$C_4$))$_2$, —COO-alkyl($C_1$–$C_4$), —CO-phenyl or —SO$_2$-phenyl groups, with the proviso that at least one of the substituents $X_1$–$X_6$ is a fluorine atom, can be prepared in an advantageous manner by reacting 1 mol of a benzil of the abovementioned formula (1) in which $X_1$–$X_6$ and $R_1$, $R_2$, $R_3$ and $R_4$ have the meanings mentioned, with the proviso that at least one of the substituents $X_1$–$X_6$ is a chlorine atom, with from about 0.8 to about 2.5 mol of potassium fluoride, rubidium fluoride, cesium fluoride or tetraalkyl ($C_1$–$C_{18}$)-ammonium fluoride or mixtures thereof per chlorine atom to be exchanged at temperatures of from about 100° to about 280° C., preferably from about 160° to about 240° C., in the absence or presence of a phase transfer catalyst and in the absence or presence of a dipolar aprotic or nonpolar solvent.

The dipolar aprotic solvents employed in the process according to the invention may be sulfolane (tetramethylene sulfone), tetramethylene sulfoxide (TMSO), N,N-diethylacetamide, N,N-dimethylacetamide (DMAc), N,N-dimethylformamide (DMF), N-methylpyrrolidone (NMP), dimethyl sulfoxide (DMSO), dimethyl sulfone, diphenyl sulfoxide, diphenyl sulfone, tetramethylurea, tetra-n-butyl urea, 1,3-dimethylimidazolidin-2-one (DMI) or mixtures thereof.

Examples of suitable nonpolar solvents are chloronapthalene, dichlorobenzene, toluene or xylenes.

The fluoride salts employed are potassium, rubidium, cesium or tetraalkyl($C_1$–$C_{18}$)-ammonium fluoride or mixtures thereof in amounts of from about 0.8 to about 2.5 mol of fluoride per chlorine atom to be exchanged, preferably from about 0.9 to about 1.5 mol and particularly preferably from about 1.0 to about 1.2 mol. Potassium fluoride and mixtures of potassium fluoride and cesium fluoride are preferred; potassium fluoride is particularly preferred. The process according to the invention permits the use of a spray-dried fluoride salt, although this is not necessary to achieve good results.

The process according to the invention can be carried out either with or without the addition of a phase transfer catalyst. However, in some cases the use of phase transfer catalysts enables virtually quantitative and considerably accelerated conversion. Suitable phase transfer catalysts are quaternary ammonium or phosphonium compounds such as tetraalkyl($C_1$–$C_{18}$)-ammonium chlorides, bromides or fluorides, tetraalkyl ($C_1$–$C_{18}$)-phosphonium chlorides or bromides, tetraphenylphosphoniumchloride or bromide, ((phenyl)$_m$(alkyl($C_1$–$C_{18}$)$_n$)-phosphonium chlorides or bromides, where m=1 to 3, n=3 to 1 and m+n=4, and also crown ethers such as, for example, 18-crown-6, and dialkylaminopyridinium salts or mixtures of these compounds. These substances are employed in amounts of from about 0.01 to about 50 mol percent, preferably between about 0.5 and about 10 mol percent and particularly preferably between about 1 and about 5 mol percent, based in each case on the benzil to be fluorinated. If tetraalkyl($C_1$–$C_{18}$)-ammonium fluoride is used as the fluoride salt, then the separate addition of a phase transfer catalyst is unnecessary, because the fluoride salt itself is already such a catalyst and can thus be employed in stoichiometric or larger amounts.

Furthermore, oligo- or polyethylene glycol dimethyl ethers can be used as phase transfer catalysts. The number of glycol units in these compounds may be from n=4 (tetraethylene glycol dimethyl ether) to about n=150, but it is preferred to employ ethers whose degree of polymerization is between about n=4 and about n=25. The optimum amount of these glycol ethers which is to be employed is between about 0.5 percent by mass and about 200 percent by mass, preferably between about 5 and about 100 percent by mass and particularly preferably between about 10 and about 50 percent by mass, based in each case on the mass of the fluoride salt employed. The particular advantage in using these compounds is that depending on the quantity in which they are employed, less solvent can be used, since the glycol ethers are always liquid at the reaction temperature.

It is also possible to employ mixtures of these ammonium compounds, phosphonium compounds, pyridinium compounds, crown ethers and glycol ethers.

In the case where the starting materials employed contain water, the reaction mixture can be dried by partial distillative removal of a component which has a higher boiling point than water. This drying can also be achieved by distilling off a component which forms an azeotrope with water. If the starting materials contain only small amounts of water or if readily volatile decomposition products are formed during the reaction, they can be removed by adding a solvent with a boiling point lower than that of the product. In this case this solvent is then distilled off from the reaction mixture during the reaction, for example via a water separator.

The process can be carried out either at atmospheric pressure or at subatmospheric or superatmospheric pressure.

The process according to the invention is particularly suitable for preparing the fluorinated benzils 2,2',4,4'-tetrafluorobenzil and 3,3'-dichloro-4,4'-difluorobenzil, which have not previously been described, from the corresponding 2,2',4,4'-tetrachlorobenzil and 3,3',4,4'-tetrachlorobenzil, respectively, by chlorine-fluorine exchange reaction.

The process according to the invention is not restricted to the reaction of symmetrical benzils; asymmetric benzils can be fluorinated analogously.

Benzils which are included under the abovementioned formula (1) and at the same time are to be regarded as new include 2-chloro-4,5-difluorobenzil, 2,2'-dichloro-4,4',5,5'-tetrafluorobenzil, 2,2',4,4',5,5'-hexafluorobenzil and 2,4,5-trifluorobenzil. The symmetrical starting materials employed in the process can be prepared, as known from the literature (J. Org. Chem. 23 (1958) 1539–1541), from the corresponding benzaldehydes by benzoin condensation and subsequent oxidation. Examples of new starting compounds are 3,3',4,4'-tetrachlorobenzil and 2,2',4,4'-tetrachlorobenzil. If asymmetric benzils are required as starting compounds, then they can be prepared not only by benzoin condensation with subsequent oxidation but also, for example, by acylation/oxidation steps, and subsequently reacted in accordance with the invention.

In addition to the preparation process described above, the invention relates to the compounds of the formula

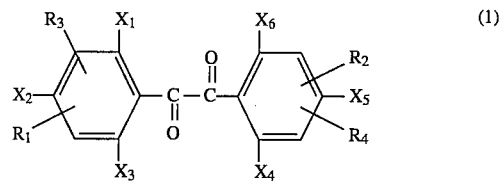

in which $X_1$, $X_2$, $X_3$, $X_4$, $X_5$, $X_6$, $R_1$, $R_2$, $R_3$ and $R_4$ have the meanings given earlier above, with the exception of the known compounds 4-fluorobenzil (CAS No. 3834-66-0), 2-fluorobenzil (CAS No. 3834-65-0), 4,4'-difluorobenzil (CAS No. 579-39-5), 2,2'-difluorobenzil (CAS No. 573-43-3), 4-fluoro-3'-bromobenzil (CAS No. 135 262-76-9), 4-fluoro-3'-nitrobenzil (CAS No. 135 262-75-8), 4-fluoro-4'-methoxybenzil (CAS No. 100 072-86-4) and decafluorobenzil (CAS No. 19 555-07-8).

The examples below illustrate the process without restricting it to them.

EXAMPLE 1

55.8 g (0.2 mol) of 4,4'-dichlorobenzil and 11 g of tetraphenylphosphonium bromide are dissolved in 250 g of sulfolane. 46.4 g (0.8 mol) of potassium fluoride are suspended in the resulting solution. The reaction mixture is then heated at 180° C. for 6 h under nitrogen with vigorous stirring. The resulting reaction suspension is cooled to about 40° C. and filtered off with suction, and the mother liquor is fractionated. This yields 28.9 g (0.119 mol, 59% of theory) of a yellow solid with a boiling point of 138°–143° C./0.01 torr. The crystallization of a sample from ethanol yields yellow crystals of 4,4'-difluorobenzil, melting point 119°–121° C.

EXAMPLE 2

7 g of potassium fluoride, 20 g of chloronaphthalene, 30 ml of toluene, 4.2 g of tetraphenylphosphoniumbromide and 4.4 g of tetraethylene glycol dimethyl ether are added to 11.2 g (0.04 mol) of 4,4'-dichlorobenzil, the toluene is removed by distillation at 150° C./45 torr, and the resulting reaction suspension is heated at 205° C. for 18 h. According to GC analysis the reaction mixture contains 32% 4,4'-difluorobenzil, 42% 4-fluoro-4'-chlorobenzil (MS) and 26% 4,4'-dichlorobenzil.

EXAMPLE 3

22.4 g (0.08 mol) of 4,4'-dichlorobenzil, 14 g (0.24 mol) of potassium fluoride and 1.0 g of 18-crown-6 in 100 g of sulfolane are heated at 180° C. for 40 h under nitrogen with stirring. According to GC analysis the conversion after this time is >90%. 14.3 g (58 mmol, 72%) of 4,4'-difluorobenzil and 0.7 g (2,6 mMol, 3%) of 4-fluoro-4'-chlorobenzil are obtained by distillation in a mixture which can be separated by crystallization.

EXAMPLE 4

34.8 g (0.1 mol) of 3,3',4,4'-tetrachlorobenzil are dissolved in 100 g of sulfolane and heated at 180° C. for 6 h with 17.5 g (0.3 mol) of potassium fluoride and 1.9 g (0.01 mol) of cesium fluoride under nitrogen with vigorous stirring. The reaction mixture is cooled to about 40° C., filtered off with suction and washed once with 20 ml of sulfolane; the mother liquor is dissolved in 600 ml of water and the solution is extracted three times with 300 ml of ether; the ether phase is washed with two times 100 ml of water and dried over molecular sieve (4 Å); and the solvent is removed at up to 40° C./20 torr. This yields 34.3 g of a dark brown solid. Subsequent fractionation yields 17.3 g (0.549 mol, 55% of theory) of 3,3'-dichloro-4,4'-difluorobenzil as a yellow crystalline solid with a boiling point of 148° C./0.05 torr.

$^1$H NMR [CDCl$_3$, TMS]: δ=7.2–7.4 (m, 1H), 7.85–7.95 (m, 1H), 8.05–8.15 (m, 1H).

$^{13}$C NMR [CDCl$_3$, TMS] : δ=117.58 (d, J=21.9 Hz), 122.95 (d, J= 17.2 Hz), 129.97 (s), 130.75 (d, J=9.1 Hz), 132.92 (s), 162.43 (d, J=260.4 Hz), 190.16 (s).

EXAMPLE 5

3.5 g (0.01 mol) of 3,3',4,4'-tetrachlorobenzil, 1.2 g (0.02 mol) of potassium fluoride, 0.5 g of tetraphenylphosphonium bromide and 1.0 g of benzophenone (internal standard) in 20 g of sulfolane are heated at 180° C. for 4 h with stirring in an inert gas atmosphere (nitrogen). According to GC analysis the reaction mixture contains— based on the 3,3', 4,4'-tetrachlorobenzil employed—44% 3,3'-dichloro-4,4'-difluorobenzil, 23% 3,4,4'-trichloro- 3'-fluorobenzil and 13% 3,3',4,4'-tetrachlorobenzil.

EXAMPLE 6

34.8 g (0.1 mol) of 2,2',4,4'-tetrachlorobenzil are dissolved in 200 g of sulfolane and are heated at 180° C. for 12 h under nitrogen with 50.4 g (0.9 mol) of potassium fluoride and 5.6 g (0.1 mol) of cesium fluoride. The reaction suspension is cooled to about 60° C., filtered off with suction, and the mother liquor is fractionated. This yields 16.9 g (0.0602 mol, 60% of theory) of 2,2',4,4'-tetrafluorobenzil as a yellowish solid with a boiling point of 132° C./0.5 torr.

$^1$H NMR [CDCl$_3$, TMS]: δ=6.75–7.2 (m, 2H), 8.0–8.2 (m, 1H)

$^{19}$F NMR [CDCl$_3$, CFCl$_3$]: δ=–105 (1F), –98 (1F)

$^{13}$C NMR [CDCl$_3$, TMS]: δ=104.91 (pseudo t, J= 25.64 Hz), 113.18 (d, J=22.2 Hz) 118.09 (dd J=2.2, 13.3 Hz) 133.00 (d, J=11.1 Hz) 163.98 (dd, J=13.2, 259.7 Hz) 167.50 (dd, J=12.4, 261.1 Hz) 188.61 (s).

EXAMPLE 7

Preparation of 3,3',4,4'-tetrachlorobenzil 241.3 g (1.4 mol) of 3,4-dichlorobenzaldehyde were placed in 125 ml of methanol, and 5 g of potassium cyanide in 7 g of water were added dropwise over 30 minutes under argon at 70° C. (immediate red coloration). The mixture was refluxed at this temperature for 4 h. The mixture was cooled, after which a clear red solution was obtained. 100 g of solvent were removed on a rotary evaporator to leave 293.8 g of a tough vitreous residue. The residue was admixed with 600 ml of toluene and heated at 60° C. with stirring. The suspension was then filtered at 45° C. and the filter cake was washed 2 times with 100 ml of toluene. Insoluble material was filtered off after 24 h and the filtrate was extracted by shaking three times with 200 ml of 20% strength sodium hydrogen sulfite solution. The solution was concentrated in vacuo to leave 194.1 g of residue. 140 g of the residue were placed in a vessel at 98° C. and 140 ml of 70% strength nitric acid were added dropwise to it over 2 h. After dilution at boiling temperature with 140 g of water, the mixture was allowed to cool slowly. After having cooled to 0° C., the mixture was filtered and washed with 200 g of water. This yielded 144.2 g of crude product which was recrystallized from 400 ml of ethanol. This yielded 54.4 g (0.156 mol, 31%) of 3,3',4,4'-tetrachlorobenzil and a further 24.4 g (0.07 mol, 14%) of this yellow compound in the form of crystal needles by concentration of the mother liquor. It was possible to improve the melting point of the product fractions by multiple recrystallization, from ethanol, from 165°–167.5° C. to 193°–198° C.

MS M/z (%)=74 (11), 109 (19), 145 (31), 147 (21), 173 (100), 175 (70), 177 (12), 346 (0.9), 348 (Me, 1.1).

EXAMPLE 8

Preparation of 2,2',4,4'-tetrachlorobenzil 482.5 g (2.8 mol) of 2,4-dichlorobenzaldehyde were placed in 250 ml of methanol, and 10 g of potassium cyanide in 14 g of water were added dropwise under argon at 68° C. over 1.5 h. The clear red solution was maintained for a further 2 h at this temperature, and then as much of the methanol as possible was removed at 95° C. in vacuo. The residue (493.1 g) was heated to 80° C. and poured into 1 l of toluene. The resulting solution was extracted by shaking with 2 times 200 ml of 20% strength sodium hydrogen sulfite solution. The extracts were then filtered for better phase separation and the organic phase was separated off. The toluene was removed in vacuo to leave 440.8 g of crude product as a tough vitreous residue.

244.0 g of this residue were heated to 100° C., and 250 ml of 70% strength nitric acid were added dropwise over 2 h. The mixture was then diluted with 100 g of water and cooled, and the supernatant liquid was decanted (255.1 g of crude product). The crude product was purified by recrystallization from ethanol. This yielded 145.5 g (0.42 mol, 54%) of pale yellow 2,2',4,4'-tetrachlorobenzil with a melting point of 157.5°–160.5° C. By concentrating the mother liquor it was possible to isolate a further 23.4 g (67 mmol, 9%) of product. By multiple recrystallization from ethanol, pure 2,2',4,4'-tetrachlorobenzil with a melting point of 161° C. was obtained.

MS m/z (%)=50 (4.5), 74 (15.5), 84 (4), 109 (23), 145 (27), 147 (18), 173 (100), 175 (72), 177 (13), 313 (2 3), 348 (M$^+$, 0.5)

We claim:
1. A compound of the formula

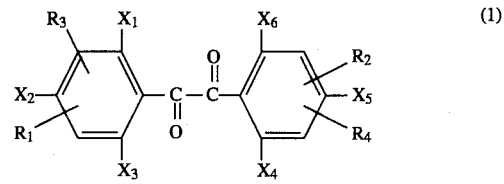

(1)

in which four X$_1$ to X$_6$ and R$_1$ to R$_4$ are chlorine or in which at least one, but less than ten, of the substituents X$_1$ to X$_6$ is a fluorine atom, and the remaining substituents X$_1$ to X$_6$ and the substituents R$_1$ to R$_4$ are hydrogen, fluorine, bromine, C$_1$– C$_{10}$-alkyl, phenyl or naphthyl which are unsubstituted or substituted by fluorine, chlorine, or bromine or by C$_1$–C$_4$-alkyl, cyano, —CHO, or CF$_3$, or one of the following groups for reducing the electron density: nitro, cyano, —CHO, —COCl, —COF, —CF$_3$, —SO$_2$—, alkyl(C$_1$–C$_4$) , —SO$_2$F, —SO$_2$Cl, or —CO-phenyl groups; wherein:

at least one of the substituents X$_1$ to X$_6$ and R$_1$ to R$_4$ is chlorine, or at least three, but less than ten, of X$_1$ to X$_6$ and R$_1$ to R$_4$ are fluorine, or if X$_2$ is fluorine and one of X$_4$ to X$_6$ and R$_2$ and R$_4$ is bromine or nitro and the remaining substituents $X_1$ to $X_6$ and $R_1$ to $R_4$ are hydrogen, the bromine or nitro substituent is positioned ortho or para to the di-carbonyl substituent, or if one or two of $X_1$ to $X_6$ and $R_1$ to $R_4$ is or are fluorine and the remaining substituents $X_1$ to $X_6$ and $R_1$ to $R_4$ are hydrogen, at least one fluorine substituent is positioned to the dicarbonyl substituent, or if one of $X_1$ to $X_3$ and $R_1$ and $R_3$ is fluorine and one of $X_4$ to $X_6$ and $R_2$ and $R_4$ is methoxy and the remaining substituents $X_1$ to $X_6$ and $R_1$ to $R_4$ are hydrogen, at least one of the fluorine or methoxy substituents is positioned ortho or meta to the di-carbonyl substituent.

2. A compound of the formula

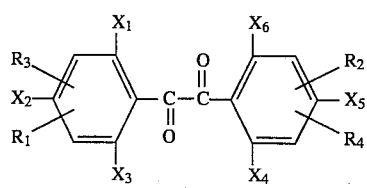

in which $X_1$, $X_2$, $X_3$, $X_4$, $X_5$, $X_6$, $R_1$, $R_2$, $R_3$, and $R_4$ have the meanings mentioned in claim 22, with the exception of the compounds 4-fluorobenzil, 2-fluorobenzil, 4,4'-difluorobenzil, 2,2'-difluorobenzil, 4-fluoro-3'-bromobenzil, 4-fluoro-3'-nitrobenzil, 4-fluoro-4'-methoxybenzil and decafluorobenzil.

3. A compound of claim 1 of the formula

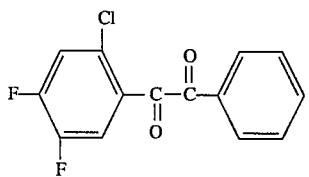

4. A compound of claim 1 of the formula

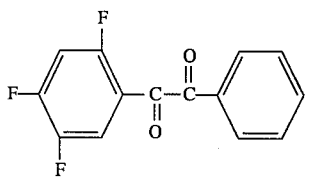

5. A compound of claim 1 of the formula

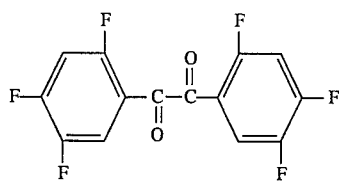

6. A compound of claim 1 of the formula

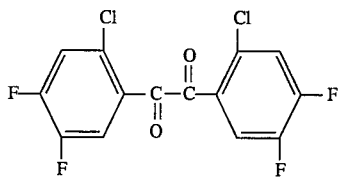

7. A compound of claim 1 of the formula

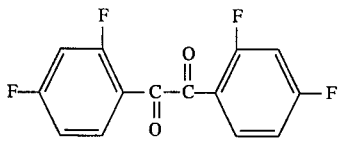

8. A compound of claim 1 of the formula

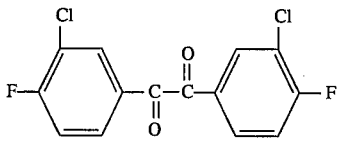

9. A compound of claim 1 of the formula

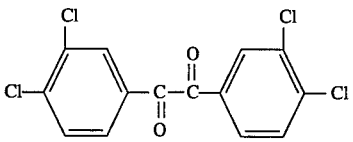

10. A compound of claim 1 of the formula

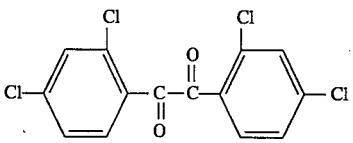

\* \* \* \* \*